(12) United States Patent
Tass

(10) Patent No.: US 10,722,711 B2
(45) Date of Patent: Jul. 28, 2020

(54) DEVICE FOR NON-INVASIVE NEURO-STIMULATION BY MEANS OF MULTICHANNEL BURSTS

(71) Applicant: Peter Alexander Tass, Tegernsee (DE)

(72) Inventor: Peter Alexander Tass, Juelich (DE)

(73) Assignee: Peter Alexander Tass, Tegernsee (DE)

( * ) Notice: Subject to any disclaimer, the term of this patent is extended or adjusted under 35 U.S.C. 154(b) by 297 days.

(21) Appl. No.: 15/542,674

(22) PCT Filed: Jan. 29, 2016

(86) PCT No.: PCT/EP2016/051896
§ 371 (c)(1),
(2) Date: Jul. 11, 2017

(87) PCT Pub. No.: WO2016/120435
PCT Pub. Date: Aug. 4, 2016

(65) Prior Publication Data
US 2018/0001088 A1    Jan. 4, 2018

(30) Foreign Application Priority Data
Jan. 30, 2015    (DE) .................. 10 2015 101 371

(51) Int. Cl.
*A61N 1/36*    (2006.01)
*A61B 5/00*    (2006.01)
(Continued)

(52) U.S. Cl.
CPC ...... *A61N 1/36031* (2017.08); *A61B 5/04001* (2013.01); *A61B 5/048* (2013.01);
(Continued)

(58) Field of Classification Search
CPC .............. A61N 2/00–12; A61N 1/0456; A61N 1/0551; A61N 1/18–445
See application file for complete search history.

(56) References Cited

U.S. PATENT DOCUMENTS

| 2013/0041296 A1 | 2/2013 | Tass et al. |
| 2013/0090519 A1 | 4/2013 | Tass et al. |
| (Continued) | | |

FOREIGN PATENT DOCUMENTS

| DE | 10 2008 039 387 A1 | 3/2010 |
| DE | 10 2009 025 407 A1 | 12/2010 |
| (Continued) | | |

OTHER PUBLICATIONS

E. Huang et al.: A confidence limit for the empirical mode decomposition and Hilbert spectral analysis, Proceedings of the Royal Society of London Series A, 459, 2317-2345 (2003).
(Continued)

*Primary Examiner* — Catherine B Kuhlman
(74) *Attorney, Agent, or Firm* — Arent Fox LLP

(57) ABSTRACT

A device is provided for the stimulation of neurons that includes a non-invasive stimulation unit to generate stimuli in multiple stimulation channels, where the stimulation unit stimulates a neuron population in the brain and/or spinal cord of a patient in different locations for each of the stimulation channels. Moreover, the device includes a control unit that controls the stimulation unit to generate repetitive bursts in each of the stimulation channels, where each of the bursts includes multiple stimuli and is designed so that they do not reset the phase of the neuronal activity of the respective stimulated neurons.

20 Claims, 6 Drawing Sheets

(51) Int. Cl.
- *A61N 5/06* (2006.01)
- *A61N 2/00* (2006.01)
- *A61N 2/02* (2006.01)
- *A61B 5/048* (2006.01)
- *A61H 23/02* (2006.01)
- *A61B 5/04* (2006.01)
- *A61H 23/00* (2006.01)
- *A61N 7/00* (2006.01)
- *A61B 5/11* (2006.01)
- *A61B 5/0488* (2006.01)
- *A61B 5/053* (2006.01)
- *A61N 1/04* (2006.01)

(52) U.S. Cl.
CPC .......... *A61B 5/4836* (2013.01); *A61B 5/7253* (2013.01); *A61H 23/00* (2013.01); *A61H 23/0236* (2013.01); *A61N 1/36025* (2013.01); *A61N 2/002* (2013.01); *A61N 2/006* (2013.01); *A61N 2/02* (2013.01); *A61N 5/0622* (2013.01); *A61N 7/00* (2013.01); *A61B 5/04008* (2013.01); *A61B 5/04014* (2013.01); *A61B 5/0488* (2013.01); *A61B 5/0531* (2013.01); *A61B 5/1114* (2013.01); *A61B 2562/0219* (2013.01); *A61H 23/0218* (2013.01); *A61H 23/0245* (2013.01); *A61H 2201/10* (2013.01); *A61H 2201/1223* (2013.01); *A61H 2201/1652* (2013.01); *A61H 2201/5007* (2013.01); *A61H 2230/085* (2013.01); *A61H 2230/505* (2013.01); *A61H 2230/605* (2013.01); *A61H 2230/655* (2013.01); *A61N 1/0456* (2013.01); *A61N 1/36014* (2013.01); *A61N 2005/0626* (2013.01); *A61N 2005/0648* (2013.01); *A61N 2007/0026* (2013.01)

(56) References Cited

U.S. PATENT DOCUMENTS

2014/0336547 A1  11/2014 Tass et al.
2015/0018898 A1* 1/2015 Tass .................. A61N 1/36064
                                                              607/62
2015/0297444 A1* 10/2015 Tass .................. A61N 1/36025
                                                              601/47
2017/0259068 A1* 9/2017 Tass .................... A61N 1/0531

FOREIGN PATENT DOCUMENTS

DE    10 2010 016 461 A1   10/2011
DE    10 2012 002 437 A1   8/2013
DE       102012002436 A1   8/2013
WO     WO 2010/043413 A1   4/2010
WO     WO-2013117655 A1 *  8/2013  ......... A61N 1/36025
WO     WO-2013117656 A2 *  8/2013  ......... A61N 1/36064

OTHER PUBLICATIONS

A. N. Silchenko, I. Adamchic, C. Hauptmann, P. A. Tass: Impact of acoustic coordinated reset neuromodulation on effective connectivity in a neural network of phantom sound. Neuroimage 77, 133-147 (2013).

I. Adamchic, B. Langguth, C. Hauptmann, P. A. Tass: Abnormal brain activity and cross-frequency coupling in the tinnitus network. Frontiers in Neuroscience 8, 284 (2014).

I. Adamchic, T. Toth, C. Hauptmann, P. A. Tass: Reversing pathological increased EEG power by acoustic CR neuromodulation. Human Brain Mapping 35, 2099-2118 (2014).

N. E. Huang et al.: The empirical mode decomposition and the Hilbert spectrum for nonlinear and non-stationary time series analysis. Proc. R. Soc. A: Math. Phys. Eng. Sci. 454:903-995 (1998).

P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012).

P. A. Tass: Transmission of stimulus-locked responses in two coupled phase oscillators. Phys. Rev. E 69, 051909-1-24 (2004).

W. C. Clapp, I. J. Kirk, J. P. Hamm, D. Shepherd, T. J. Teyler: Induction of LTP in the human auditory cortex by sensory stimulation. European Journal of Neuroscience, vol. 22, 1135-1140 (2005).

* cited by examiner

DEVICE FOR NON-INVASIVE NEURO-STIMULATION BY MEANS OF MULTICHANNEL BURSTS

CROSS-REFERENCE TO RELATED APPLICATIONS

This application is a National Stage entry of International Application No. PCT/EP2016/051896, filed on Jan. 29, 2016, which claims priority to German Application No. 10 2015 101 371.1, filed on Jan. 30, 2015, the contents of each of these priority applications are hereby incorporated by reference in their entirety.

TECHNICAL FIELD

The invention relates to an apparatus and to a method for a non-invasive neuro-stimulation by means of multichannel bursts.

BACKGROUND

With regard to patients suffering from neurological or psychiatric diseases, e.g. Morbus Parkinson, essential tremors, dystonia, functional interferences following a stroke, migraine, obsessive-compulsive disorder, epilepsy, tinnitus, schizophrenia, depression, borderline personality disorders such as well as irritable bowel syndrome, groups of neural cells are active in described regions of the brain in a pathological synchronous way. In this case a large number of neurons form synchronous action potentials, this means the associated neurons stimulate excessively synchronously. In contrast to this the neurons of healthy people trigger in a qualitatively different way in these regions of the brain, e.g. in an uncorrelated manner.

Having regard to Morbus Parkinson the pathological synchronous activity in the thalamus and in the basal ganglia changes the neuronal activity in different regions of the brain e.g. in regions of the cerebral cortex, such as the primary motor cortex. In this connection the pathological synchronous activity in the region of the thalamus and the basal ganglia, for example, impinges its rhythm onto the regions of the cerebral cortex in such a way that finally the muscles controlled by the regions develop a pathologic activity, e.g. a rhythmic tremor. Having regard to chronic subjective tinnitus, the pathological synchronous activity takes place in a network of auditory as well as non-auditory regions of the brain.

Having regard to patients with brain diseases and spinal cord diseases which are characterized by an excessively synchronized neuronal activity, certain spatial time stimulation patterns determined non-invasively, in particular the "Coordinated Reset" stimulation (CR stimulation) are applied in order to achieve a permanent relief. The non-invasive CR stimulation can be realized by means of different stimulation modes:

(i) by way of sensory stimulation, this means by way of physiological stimulation of receptors, such as e.g. acoustic stimulation of the inner ear, visual stimulation of the retina or mechanical stimulation (e.g. vibro-tactile stimulation) or thermal stimulation of skin receptors, subcutaneous receptors, muscle receptors and tendon receptors.

(ii) by way of stimulating peripheral nerves (and the associated receptors) e.g. by way of electric current (e.g. transcutaneous electro-stimulation) by means of magnetic fields (transdermal magnetic stimulation) or by means of ultrasound; and (iii) by way of stimulation of the brain or spinal cord, e.g. by way of electrical current (e.g. external cranial respectively transcranial nerve stimulation), by means of magnetic fields (e.g. transcranial magnetic stimulation) or by means of ultrasound.

For the treatment of chronic subjective tonal respectively narrow band tinnitus, the acoustic CR stimulation is used. For this purpose therapeutic sounds are matched to the dominant sound of the tinnitus and are applied in the sense of the CR stimulation in order to achieve a prolonged desynchronization of the pathological synchronous activity significantly outlasting a switching off of the simulation respectively even achieve a continuous desynchronization of the pathological synchronous activity. The acoustic CR stimulation for the treatment of the tinnitus brings about a significant and markedly pronounced decrease of the symptoms (cf. P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012)), a significant reduction of the pathological neuronal synchronization in a network of auditory and non-auditory regions of the brain (cf. P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012); I. Adamchic, T. Toth, C. Hauptmann, P. A. Tass: Reversing pathological increased EEG power by acoustic CR neuromodulation. Human Brain Mapping 35, 2099-2118 (2014)), a significant reduction of the pathological interaction between different regions of the brain in the same (cf. A. N. Silchenko, I. Adamchic, C. Hauptmann, P. A. Tass: Impact of acoustic coordinated reset neuromodulation on effective connectivity in a neural network of phantom sound. Neuroimage 77, 133-147 (2013)), as well as in different frequency ranges (cf. I. Adamchic, B. Langguth, C. Hauptmann, P. A. Tass: Abnormal brain activity and cross-frequency coupling in the tinnitus network. Frontiers in Neuroscience 8, 284 (2014)).

In an analog way Parkinson's disease can be treated by means of vibratory tactile CR stimulation. Further indications are represented by e.g. epilepsy, functional disorders following a stroke, chronic pain syndrome (by means of vibro-tactile and/or thermal CR stimulation), migraine (e.g. by means of visual CR stimulation). Furthermore, these diseases can be treated with transcranial magnetic stimulation and/or direct electrical stimulation of the brain or direct brain stimulation by means of ultrasound.

With respect to the stimulation modalities (i) to (iii) listed above for the stimulation with stimuli of reduced intensity shall be effected, reasons are listed in the following in order to avoid side effects and/or to increase the therapeutic effectiveness:

(i) Having regard to the sensory stimulation it is important to even be able to achieve the desired stimulation effect (e.g. a phase reset of the pathological synchronized oscillatory activity in the brain or spinal cord) at an as low as possible stimulation strength. E.g. hearing impaired patients have to be treated typically with respect to the acoustic CR stimulation for the treatment of the tinnitus. The stimulation with loud sounds can damage the inner ear, complicate the communication with others as well as cover up warning signals (e.g. a vehicle horn, bicycle bell) or be perceived by the patient as being markedly unpleasant as a consequence of the threshold running fairly close to the hearing threshold considered as unbearable and the loud stimulation can also be heard by the environment of the patient and thus can be perceived as annoying. Having regard to the visual CR stimulation, in particular unpleasant blinding effects can be brought about having respect to migraine patients. Having regard to the mechanical stimulation, e.g. vibrato-tactile or thermal CR stimulation of patients with chronical pain syndrome (e.g. Morbus Sudeck or neuralgia). Even the slightest of touches or warmth stimuli can be perceived as unpleasant or even as painful. When in such cases e.g. a treatment has to be performed via the contralateral extremity or via half of the face or half of the body, the effect of stimulation as a consequence of the application in the healthy half of the body is not strongly pronounced. As a whole it is very advantageous with respect to the sensory CR stimulation when a stimulation having a very small stimulation strength can be carried out, as sensory stimuli (e.g. sounds, brightness deviations of transmission pair of glasses etc.) can interfere with the physiological processing of stimuli.

(ii) In order to be able to stimulate the peripheral nerves in an as focal manner as possible during the electric or magnetic stimulation and in order to avoid side effects that are brought about by way of the co-stimulation of adjacent structures (e.g. muscle contraction, pain sensation etc.) it is important to use as small as possible stimulation strengths.

(iii) Both the electrical and also the magnetic stimulation of the brain or spinal cord are not very focal. In particular the direct electric stimulation of the brain itself in the most favorable case of the stimulation over a plurality of small electrodes and on use of head models demanding in effort and cost besides a focal strong stimulation also lead to a co-stimulation of extensive regions of the brain that particularly for chronic irritation should be avoided or reduced without fail. In the same way the ultrasound stimulation should be limited to the actual target regions in the brain.

In all of these cases it is thus required to treat using an as small as possible stimulation strength in order to reduce the undesired co-stimulation of non-target regions. This however frequently leads thereto that the treatment is not sufficiently effective.

Moreover, the stimulation effect should be as sustainable as possible in order to ensure the compliance, this means the cooperation and "loyalty to treatment" of the patient.

SUMMARY

For this reason it is the object of the invention to provide an apparatus as well as a method that respectively enable the achievement of good, robust and in particular long lasting therapeutic effects even having regard to very small stimulation strengths.

The subject-matter of the invention based on this object is satisfied by the features of the independent claims. Advantageous embodiments and designs of the invention are stated in the subordinate claims.

BRIEF DESCRIPTION OF THE DRAWINGS

The invention will be described in the following in detail in an exemplary manner with reference to the drawings. In the drawing there is shown.

DETAILED DESCRIPTION

Figure 1:
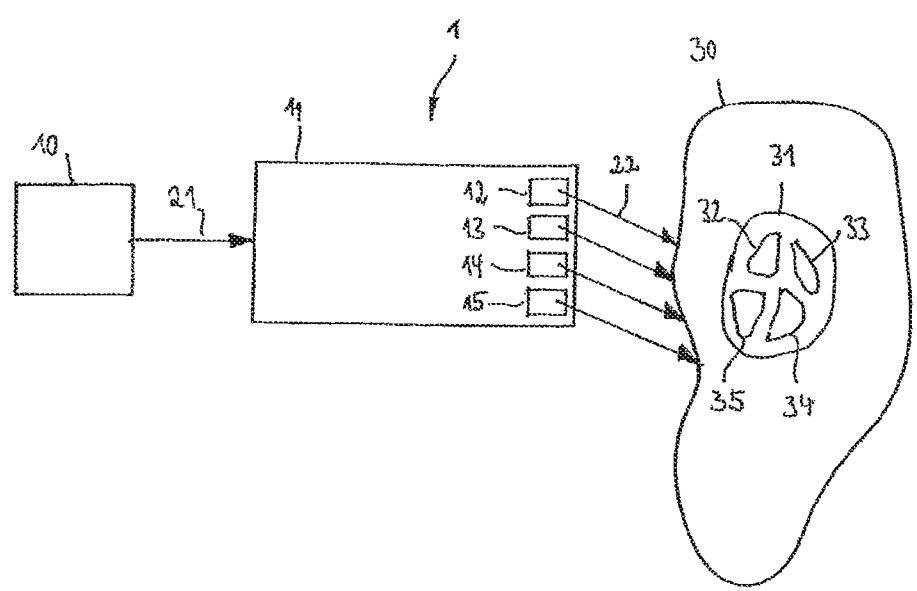
FIG. 1 illustrates a schematic diagram of an apparatus for the suppression of a pathological synchronous and oscillatory neuronal activity and in particular for desynchronization of neurons with a pathological synchronous and oscillatory activity in accordance with a first embodiment.

An apparatus 1 for the stimulation of neurons having a pathological synchronous and oscillatory neuronal activity is illustrated schematically in FIG. 1. The apparatus 1 is composed of a control unit 10 and a stimulation unit 11 that stimulates neurons in the brain and/or the spinal cord 30 of a patient via a plurality of stimulation channels. Each stimulation channel enables the stimulation of a different target region of the brain and/or of the spinal cord of the patient, wherein the target regions associated with the stimulation channels do not necessarily have to be disjunct from one another, this means completely separated from one another, but can also overlap one another. By way of example the stimulation via four stimulation channels 12, 13, 14 and 15 is illustrated in FIG. 1. However, they can naturally also be stimulated via a different number of stimulation channels.

During the operation of the apparatus 1 the control unit 10 carries out a control of the stimulation unit 11. For this purpose the control unit 10 generates control signals 21 that are received by the stimulation unit 11.

The stimulation unit 11 generates stimuli 22 by means of the control signals 21 in the stimulation channels 12 to 15 that are administered to the patient. The stimuli 22 can be sensory stimuli, e.g. acoustic stimuli, visual stimuli, tactile stimuli, vibratory stimuli, thermal stimuli, olfactory stimuli, gustatory stimuli, transcutaneous electrical stimuli, transcutaneous magnetic stimuli, transcranial electric stimuli and/or transcranial magnetic stimuli and/or ultrasound stimuli. In particular tactile stimuli and vibratory stimuli 22 are also applied together and are then referred to as vibrato-tactile stimuli. The stimuli 22 can be perceived by the patient, in particular can be consciously perceived. The parameters of stimuli 22 are set by the control unit 10.

The stimulation unit 11 and in particular also the control unit 10 are non-invasive units, this means that during the operation of the apparatus 1 they are present outside of the body of the patient and are not operatively implanted into the body of the patient.

Figure 3:
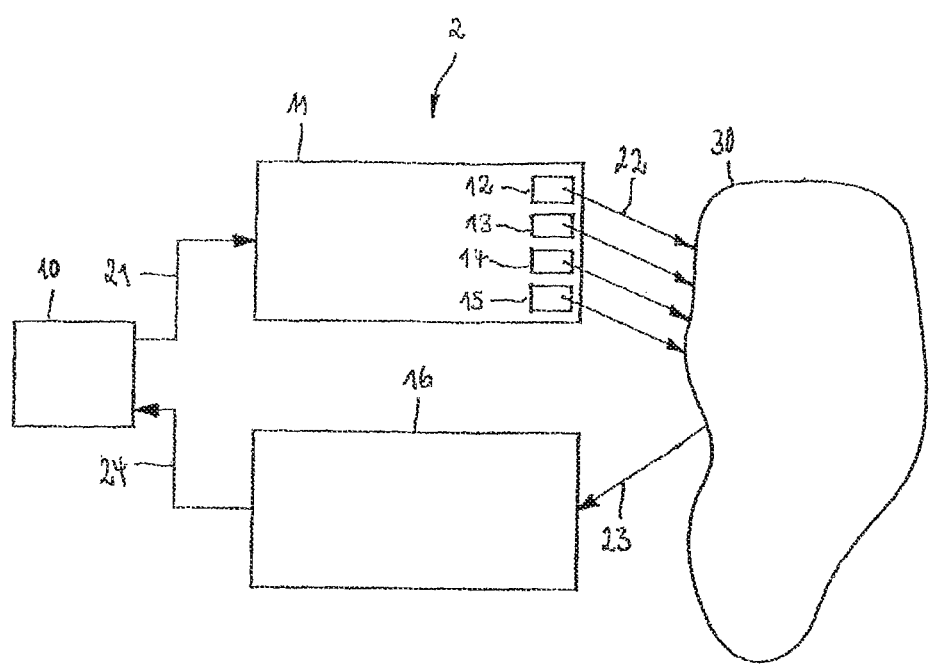
FIG. 3 illustrates a schematic diagram of an apparatus for the suppression of a pathological synchronous and oscillatory neuronal activity and in particular for desynchronization of neurons with a pathological synchronous and oscillatory activity in accordance with a second embodiment.

The apparatus 1 and the apparatus 2 described in the following in connection with FIG. 3 are in particular used for the treatment of neurological or psychiatric diseases, e.g. Morbus Parkinson, essential tremor, tremor as a consequence of multiple scleroses as well as other pathological tremors, dystonia, epilepsy, depression, motor disorders, cerebellar diseases, obsessive-compulsive disorder, dementia, Morbus Alzheimer, Tourette syndrome, autism, functional interferences following a stroke, spastics, tinnitus, sleeping disorders, schizophrenia, irritable colon syndrome, addicted disorders, borderline personality disorders, attention deficit disorders, attention deficit hyperactivity disorders, compulsive gambling, neuroses, bulimia, anorexia, eating disorders, burnout syndrome, fibromyalgia, migraine, cluster headaches, general headaches, neuralgia, ataxia, tic disorder or hypertonia, as well as further illnesses that are characterized by a pathological increased neuronal synchronization.

The previously mentioned illnesses can be caused by an interference of the bioelectrical communication of neuron networks that are connected in specific circuits. Hereby a neuron population generates a continuous pathological neuronal activity possibly a pathological connectivity (network structure) inherent to this. In this connection a large number of neurons form synchronous action potentials, this means that the associated neurons fire excessively synchronous. In addition to this the pathological neuron population has a oscillatory neuronal activity, this means the neurons fire rhythmically. In the case of neurological or psychiatric diseases the mean frequency of the pathological rhythmic activity of the associated neuron networks approximately lies in the range of 1 to 30 Hz, but can also lie outside of this range. Having regard to healthy patients, the neurons in contrast to this trigger in qualitatively different manner, e.g. in an uncorrelated manner.

In FIG. 1 the apparatus 1 is illustrated during a stimulation of pathological neurons. At least one neuron population 31 in the brain and/or the spinal cord 30 of the patient has a pathological synchronous and oscillatory neuronal activity as described in the foregoing. The stimulation unit 11 generates sensory stimuli 22 that are received by the patient and are forwarded via the nervous system to the pathological active neuron population 31 in the brain and/or the spinal cord 30. As the pathological neuron population 31 is stimulated at different positions via the stimulation channels 12 to 15, different sub-populations of the neuron population are in this way stimulated via the stimuli 22. In FIG. 1 four such sub-populations 32 to 35 are illustrated by way of example. In the present embodiment the sub-population 32 is stimulated via the stimulation channel 12, the sub-population 33 is stimulated via the stimulation channel 13, the sub-population 34 is stimulated via the stimulation channel 14 and the sub-population 35 is stimulated via the stimulation channel 15. The respective volume of the sub-populations 32 to 35 depends on the strength of the respectively stimulated stimuli 22. The more intense the stimulation strength is, the larger the extent of the sub-population stimulated thereby is.

Figure 2:
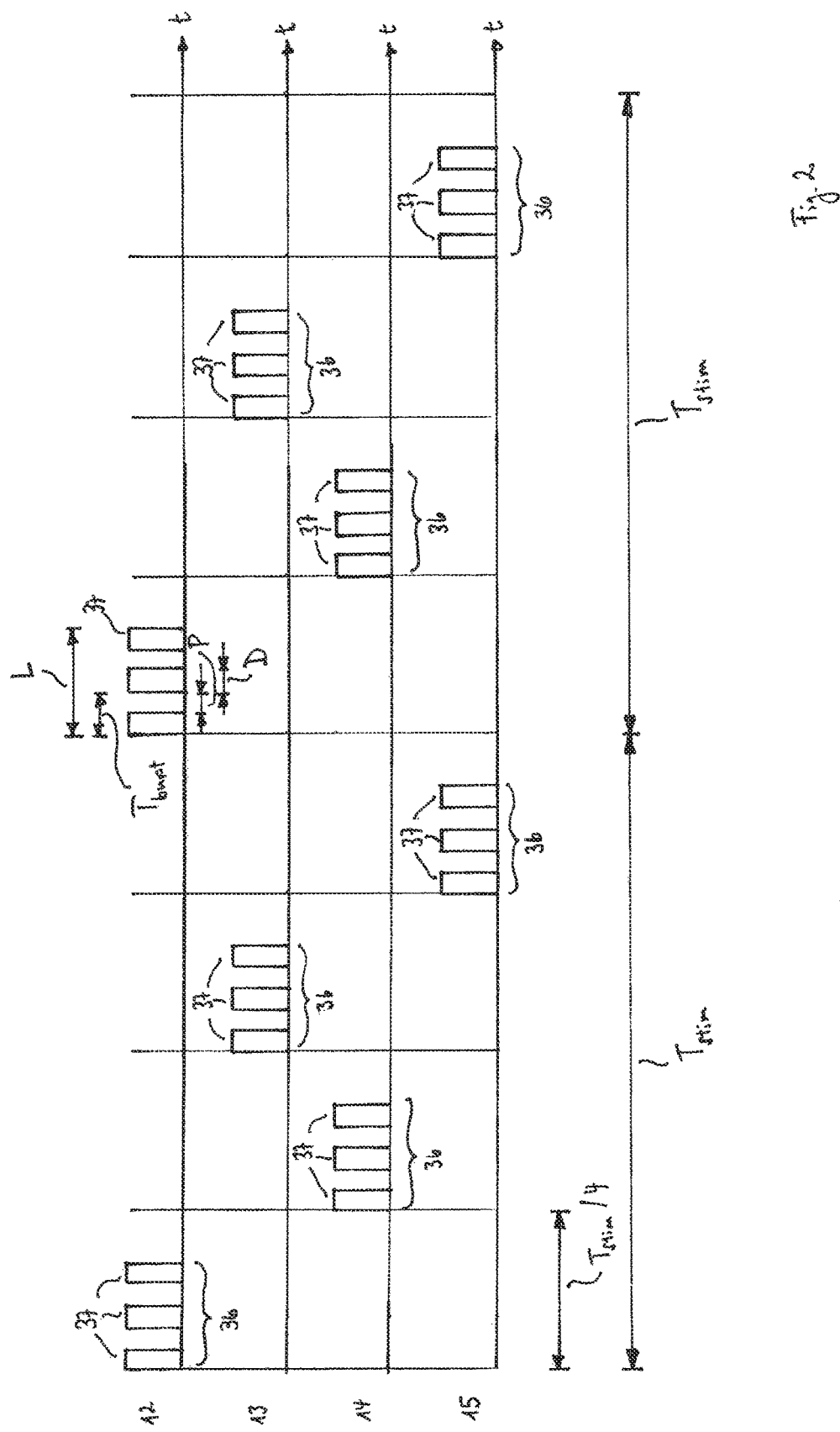
FIG. 2 illustrates a schematic diagram of a stimulation of a multi-channel burst.

In FIG. 2 the stimuli 22 generated in the stimulation channels 12 to 15 by means of the stimulation unit 11 are shown in larger detail. In accordance with an embodiment, repetitive bursts 36 are generated in the stimulation channels 12 to 15, wherein each of the bursts 36 includes a plurality of stimuli 37. The stimuli 37 are in particular individual stimuli or individual pulses. In FIG. 2 the bursts 36 generated in the stimulation channels 12 to 15 are listed underneath one another against the time t. The bursts 36 are generated in a predefined time pattern that is composed of successive cycles. Each cycle has a duration $T_{stim}$, wherein $T_{stim} = 1/f_{stim}$ is true and $f_{stim}$ is a frequency in the range of 1 to 30 Hz. In FIG. 2 two of the cycles are illustrated by way of example. Furthermore, the cycles of the length $T_{stim}$ are divided into equally long sub-cycles that respectively have a length of $T_{stim}/4$ for the embodiments illustrated in FIG. 2. Generally the length of sub-cycles is as long as the length $T_{stim}$ divided by the number of stimulation channels in which the bursts 36 are generated. If one consequently stimulates over S stimulation channels, then the duration of one of the sub-cycles amounts to $T_{stim}/S$. The pattern shown in FIG. 2 of the cycles and sub-cycles is periodically continued.

In each cycle of length $T_{stim}$ the stimulation unit 11 generates exactly one burst in each of the stimulation channels 12 to 15 and in each of the sub-cycles of the length $T_{stim}/4$ (respectively $T_{stim}/S$ in the general case), the stimulation unit 11 generates exactly one burst in exactly one of the stimulation channels 12 to 15. A sequence of four bursts 36 (respectively S bursts 36 in the general case) are generated per cycle, wherein each sequence includes exactly one burst 36 per stimulation channel.

The sequence of the stimulation channels 12 to 15 in which the bursts 36 can be generated within a sequence can be constant. Alternatively the sequence can also be varied in accordance with a predefined number of cycles. The variation of the sequence can e.g. take place stochastically or deterministically or mixed stochastic-deterministically. In the cycles shown in FIG. 2, the bursts 36 are generated in the stimulation channels 12 to 15 in the sequence 12-14-13-15.

Bursts 36 generated in time directly following one another in different stimulation channels are displaced in time by $T_{stim}/4$ in the present case with four stimulation channels (respectively $T_{stim}/S$ in the general case with S stimulation channels). In accordance with an embodiment one can deviate by e.g. up to ±5%, ±10% or ±20% from the value $T_{stim}/S$ for the delay in time between directly consecutive bursts 36. The delay in time can in particular relate to the starting point in time of the bursts 36. As long as the sequence of the stimulation channels 12 to 15 remains constant within a sequence, the bursts 36 are repeated in each of the stimulation channels 12 to 15 periodically with the frequency $f_{stim} = 1/T_{stim}$.

The bursts 36 are respectively composed of a sequence of short stimuli 37, wherein a burst 36 includes e.g. 2 to 20, in particular 3 to 9 stimuli 37. The stimuli 37 can respectively be pulses, in particular individual pulses. In this case the bursts 36 can also be considered as a pulse train. A burst 36 can have a duration L in the range of 50 ms to 200 ms. In FIG. 2, D is the duration of the individual pulses 37 and P is the pause between two stimuli 37 directly following one another within a burst 36. The period with which the stimuli 37 can be repeated within one burst 36 amounts to $T_{burst}$. The frequency $f_{burst} = 1/T_{burst}$ can lie in the range of 7 Hz to 50 Hz.

The duration D and the pause P can, but do not have to be of equal length. Furthermore, the duration D and the pause P can respectively be held constant during a burst 36; however, can also be varied within a burst 36 or from burst 36 to burst 36. For example, individual stimuli 37 of different length can be provided within a burst 36 and/or different length pauses P between the individual stimuli 37 can be provided. Furthermore, the duration D and/or the pause P can be varied from burst 36 to burst 36 within a stimulation channel and/or between stimulation channels. The variations can take place deterministically, stochastically or mixed deterministic-stochastic regularities.

The bursts 36 administered to the patient are configured in such a way that they do not bring about a resetting of the stimulated neuron population 31, this means no reset of the phase of the neuronal activity of the stimulated neurons takes place. By way of the reset the phase of the stimulated neurons would be set independent of the actual phase value to a defined phase value or close to a defined phase value, of e.g. 0°. Having regard to the stimulation used in this context the bursts 36 are configured in such a way that such a phase reset is precisely not effected. Rather the invention utilizes a different functional principle: By way of the stimulation delayed in time of the respective sub-populations, the synchronization in the respective sub-populations is slightly increased due to the delay in time. As a whole the complete neuron population 31 reacts surprisingly to this kind of stimulation in that it down regulates the mean synaptic network in a compensatory manner. In this way long lasting therapeutic effects can be generated in the course of the treatment.

In accordance with an embodiment cycles are provided in which the stimulation pauses are maintained. Thus, during n subsequent cycles of the length $T_{stim}$, as indicated in FIG. 2, bursts 36 can be generated and during the subsequent m cycles no bursts 36 are generated, wherein n and m are non-negative whole numbers. The pattern of n cycles with stimulation and m cycles without stimulation can be periodically continued.

The period $T_{stim}$ that, on the one hand, indicates the duration of a cycle, and, on the other hand, the period, with which unvarying sequences of the bursts 36 generated in a respective stimulation channel 12 to 15 is repeated can lie in the vicinity of the mean period of the pathological oscillation of the neuron population 31 with the pathological synchronous and oscillatory neuronal activity respectively they can deviate by up to ±5%, ±10% or ±20% of the mean period. Typically the frequency $f_{stim}=1/T_{stim}$ lies in the range of 1 to 30 Hz. The period of the pathological oscillation of the neuron population 31 to be stimulated can, for example, be measured by means of the measurement unit 16 described in the following, in particular by means of EEG. For this purpose, in particular the mean dominant frequency of the pathological synchronized oscillatory neuronal activity can be measured in a time window, in particular a sliding time window. However, it is also possible to use literature values or values of experience for the period of the pathological oscillation that relate to the respective disease to be treated.

Generally it can be possible to stimulate via an arbitrary number A of stimulation channels (A≥2) by means of the stimulation unit 11, however, bursts 36 do not necessarily have to be generated for a stimulation in all L stimulation channels, for example, only a selection B of the A stimulation channels can generate the bursts 36 (2≤B≤A).

By way of the stimulation carried out with the apparatus 1 a suppression and in particular a desynchronization of the pathological synchronous and oscillatory activity of the neuron population 31 is brought about albeit only a small stimulation strength. A reduction of the synaptic weight achieved by the stimulation can lead to a mis-teaching of the tendency to produce pathological synchronous activity. Furthermore, by way of the stimulation a re-organization of the connectivity of the dysfunctional neuronal networks can be achieved such that long lasting therapeutic effects can be brought about. The achieved synaptic reconstruction is of large importance for the effective treatment of neurological or psychiatric diseases.

The apparatus 1 illustrated in FIG. 1 for the stimulation of neurons with a pathological synchronous and oscillatory neuronal activity carries out a so-called "open loop" stimulation, this means a stimulation without the use of sensors that can be used for the feedback and/or the control of the stimulation.

FIG. 3 schematically shows an apparatus 2 for the stimulation of neurons with a pathological synchronous and oscillatory neuronal activity by means of which a "closed loop" stimulation can be carried out. The apparatus 2 is a further development of the apparatus 1 illustrated in FIG. 1 and likewise includes, just like apparatus 1, a control unit 10 and a non-invasive stimulation unit 11 which has the same functions as the control and stimulation units 10, 11 of the apparatus 1 described in the foregoing.

Moreover, the apparatus 2 comprises a measurement unit 16. The stimulation effects achieved by way of the stimuli 22 is monitored with the aid of the measurement unit 16. The measurement unit 16 records one or more measurement signals 23 measured at the patient, transforms these possibly into electrical signals 24 and forwards these to the control unit 10. In particular the neuronal activity in the stimulated target region can be measured by means of the measurement unit 16 or of a region connected to the target region, wherein the neuronal activity of this region correlates in a sufficiently close manner with the neuronal activity of the target region. By means of the measurement unit 16 also a non-neuronal, e.g. muscular activity or the activation of the autonomous nervous system can be measured, in as far as this is sufficiently closely correlated to the neuronal activity of the target region.

The measurement unit 16 includes one or more sensors that in particular enable a detection of the decrease or increase of the amplitude of the pathological oscillatory activity.

Non-invasive sensors can be used as sensors, e.g. chronic or intermittently used electroencephalography (EEG) or electromyography (EMG) electrodes or magnetoencephalography (MEG) sensors. The neuronal activity can also be determined by way of detection of characteristic movement patterns, such as tremor, akinesia or epileptic fits with the aid of an accelerometer or gyroscope or indirectly by way of measuring the activation of the autonomous nervous system by means of measurement of the skin resistance. Values relating to the state of mind that are input by the patient into portable devices, e.g. smartphones, can be used for the control of the stimulation success.

Alternatively, but less preferred, the sensors can be implanted into the body of the patient. Epi-cortical electrodes, deep brain electrodes for the measurement of e.g. local field potentials, subdural or epidural brain electrodes, subcutaneous EEG electrodes and sub or epidural spinal cord electrodes can serve as invasive sensors by way of example.

The control unit 10 processes the signals 24, e.g. the signals 24 can be amplified and/or filtered and analyses the processed signals 24. The control unit 10 checks the stimulation success by means of the measurement signals 23 recorded as a reaction to the application of the stimuli 22.

With the aid of the measurement signals 23 recorded by the measurement unit 16 a check can further be made whether the bursts 36 applied by the stimulation unit 11 do not reset the phase of the neuronal activity of the stimulation neurons. As described above the bursts 36 should not reset the phase of the neuronal activity of the stimulated neurons. Such an investigation can be carried out prior to the actual therapeutic stimulation with which the pathological synchronous and oscillatory activity of the neuron population 31 should be suppressed or desynchronized.

For this purpose a signal is measured by a sensor of the measurement unit 16 which sufficiently represents the activity of a sub-population stimulated via the j-th stimulation channel. One receives this signal either directly from the sub-population or via a non-invasive measurement, e.g. via EEG or MEG electrodes or an invasive measurement, e.g. via implanted electrodes, such as surface EEG or as local field potentials via depth electrodes. The signal can also be determined indirectly via the measurement of a parameter correlated with the activity of the stimulated sub-population. For this purpose, e.g. EEG signals/MEG signals/LFP signals of the neuronal activity are coupled closely to these sub-population of different neuron populations or associated electromyography signals, accelerometer signals or gyroscope signals.

As neuronal signals typically include rhythmic activity in the different frequency bands it is advantageous in such cases to determine which represents the pathological oscillatory activity of the sub-population stimulated by the j-th stimulation channel e.g. by means of band pass filtering or wavelet analysis or empirical mode decomposition of the signal $x_j(t)$.

A process, only slightly demanding in effort and cost, for excluding a phase reset by the burst consists therein in determining the averaged response to the stimuli. For this purpose a burst with identical stimulation parameters is applied at the times $\tau_1, \tau_2, \ldots, \tau_l$. The spacing between the individual bursts $\tau_{k+1} - \tau_k$ should be sufficiently large and randomized, this means not to be constant in order to avoid transient processes (cf. P. A. Tass: Transmission of stimulus-locked responses in two coupled phase oscillators. Phys. Rev. E 69, 051909-1-24 (2004)). Typically the spacings $\tau_{k+1} - \tau_k$ should lie in the range of at least the ten-fold, better the hundred-fold of the mean period of the pathological oscillation. The stimulation response averaged over all l test bursts is calculated in accordance with the following equation:

$$\bar{x}_j(t) = \frac{1}{l} \sum_{k=1}^{l} x_j(\tau_k + t) \quad (1)$$

In as far as the spacings $\tau_{k+1} - \tau_k$ between the individual bursts is sufficiently large one does not receive an averaged stimulation response in the pre-stimulation range, this means in the region before the application of a respective burst (cf. P. A. Tass: Transmission of stimulus-locked responses in two coupled phase oscillators. Phys. Rev. E 69, 051909-1-24 (2004)). A phase reset can be excluded when no averaged stimulation response can be detected, this means when in the post stimulation range, this means in the range for t>0, with t=0 representing the starting point of the respective burst, a stimulation response not different from zero is present. This can be determined by means of visual inspection. One can also have this carried out by the apparatus 2, in particular by the control unit 10, in that one considers a pre-stimulus distribution of $\bar{x}_j(t)$ or $|\bar{x}_j(t)|$d and determines a characteristic threshold value, e.g. the $99^{th}$ percentile of the pre-stimulus on distribution of $|\bar{x}_j(t)|$ or simply its maximum. If now e.g. the amount of the post-stimulus response principally exceeds this characteristic threshold value or for a pre-defined minimum duration of e.g. 20 ms, then an averaged response different from zero is present. In this case a phase reset can no longer be excluded. This means the intensity of stimulation must be reduced for so long up until the post-stimulus response does not significantly differ from a zero line. Besides this illustrated simple case in this context, that is approved of practice, also different known statistical tests for the signal analysis can be drawn upon by the person skilled in the art.

A more precise variant, but a variant more demanding in effort and cost for the investigation of whether a burst can bring about a phase reset, is made available by the analysis of the phase. For this purpose the phase $\psi_j(t)$ of $x_j(t)$ is determined. This takes place by means of a Hilbert transformation of the signal determined by means of the band pass filtering or empirical mode decomposition, with the signal representing the pathological oscillatory activity. The empirical mode decomposition enables a parameter independent determination of physiological relevant modes in different frequency regions in comparison to the band pass filtering (cf. N. E. Huang et al.: The empirical mode decomposition and the Hilbert spectrum for nonlinear and non-stationary time series analysis. Proc. R. Soc. A: Math. Phys. Eng. Sci. 454:903-995 (1998)). The combination of empirical mode decomposition with subsequent Hilbert Transformation is referred to as Hilbert-Huang-transformation (cf. N. E. Huang et al.: A confidence limit for the empirical mode decomposition and Hilbert spectral analysis, Proceedings of the Royal Society of London Series A, 459, 2317-2345 (2003)). The phase $\psi_j(t)$ can also be determined by means of wavelet analysis.

A phase reset is present when the phase $\psi_j(t)$ is set to a preferred value after a certain period of time by way of a burst (with burst starting at t=0). This means that $\{\psi_j(\tau_k+t)\}_{k=1,\ldots,l}$, of the distribution obtained by the l stimulation responses of the value of the phase $\psi_j(t)$ at the time t (relative to the start of the burst at t=0) has an accumulation point. The person of ordinary skill in the art knows several methods with which one can show that a distribution has an accumulation point (this means a peak). A common method is the determination of the phase reset index $\rho(t)$ by means of circular mean value:

$$\rho(t) = \left| \frac{1}{l} \sum_{k=1}^{l} \exp[i\psi_j(\tau_k + t)] \right| \quad (2)$$

A phase reset is present when $\rho(t)$ e.g. the maximum or the 99th percentile of the pre-stimulus distribution of $\rho(t)$ (at a point in time or within a small time window of e.g. 20 ms width) is exceeded.

In practice the analysis with the averaged responses $\bar{x}_j(t)$ has been found to be sufficient.

The bursts can be calibrated in the following manner:
1. The experienced user has corresponding values of experience that enable him to set suitable stimulation parameters in the course of a therapy or even from the start. This means a calibration can be dispensed with.
2. The stimuli can however also be calibrated, e.g. in that starting at a higher stimulation strength, the stimulation strength, e.g. (typically) the amplitude (intensity) of the individual stimuli of the burst or the number of the individual stimuli included in the burst are reduced for so long up until the burst no longer generates a phase reset. One can, for example, reduce the amplitude by 5% or 10% or 20% or even further beneath the required threshold amplitude for a phase reset.

In accordance with an embodiment, the parameters of the bursts 36 and/or the duration of the stimulation can be controlled by the control unit 10 on the basis of an analysis of the processed signals 24. For example, the duration $T_{stim}$ of the cycles, the repetition frequency $f_{burst}$ of the stimuli 37 in the bursts 36, the intensity of the stimuli 37, the duration D of the stimuli 37, the duration P of the pauses between subsequent stimuli 37, the selection of the stimulation channels, via which the stimulation takes place, as well as a stimulation controlled as required, during which one only stimulates on the presence of measured pathological markers is controlled.

The success of the stimulation can be checked in particular by means of a threshold value comparison. Depending on which signals are drawn on for the determination of the stimulation success different threshold value comparisons result. If, e.g. the pathological neuronal synchronization is measured via the sensors of the measurement unit 16, e.g. the EEG electrons, then the reduction of the synchronization by e.g. 20% in comparison to the situation without stimulation is typically sufficient in accordance with experience in order to determine a sufficient stimulation success. In accordance with an embodiment a non-sufficient stimulation success can be determined when the pathological neuronal synchronization is not reduced by at least one predefined value by way of the application of the bursts 36. If symptoms of the patient for determining the stimulation success are drawn on it depends on the kind of used clinical parameters which decrease is to be considered as a clinically relevant improvement. Such reduction values (e.g. in the sense of the so-called minimal clinically perceivable improvement) are known to the person of ordinary skill in the art.

Furthermore, the apparatuses 1 and 2 can comprise an input device which is coupled to the control unit 10 and can be operated by the patient or a person treating the patient, for example the doctor carrying out the treatment. Evaluations of the patient can be input into the input device that represent the stimulation success perceived subjectively by the patient. For example, it can be provided that one or more stimulation patterns are changed if the stimulation success perceived by the patient sinks below a predefined threshold. E.g. in such a case the repetition frequency $f_{burst}$ of the stimuli 37 in the bursts 36, the intensity of the stimuli 37, the duration D of the stimuli 37 and/or the duration P of the pauses between subsequent stimuli 37 can be varied. In particular the variation of the stimulation parameters can take place for so long up until the stimulation success perceived by the patient exceeds a further predefined threshold.

The individual components of the apparatuses 1 and 2, in particular the control unit 10, the stimulation unit 11 and/or the measurement unit 16 can be separated from one another in a constructive manner. The apparatus 1 and 2 can for this reason also be considered as systems. For carrying out its tasks the control unit 10 can include a processor, e.g. a microcontroller. The stimulation methods described herein can be stored as a software code in a memory associated with the control unit 10.

Figure 4A:
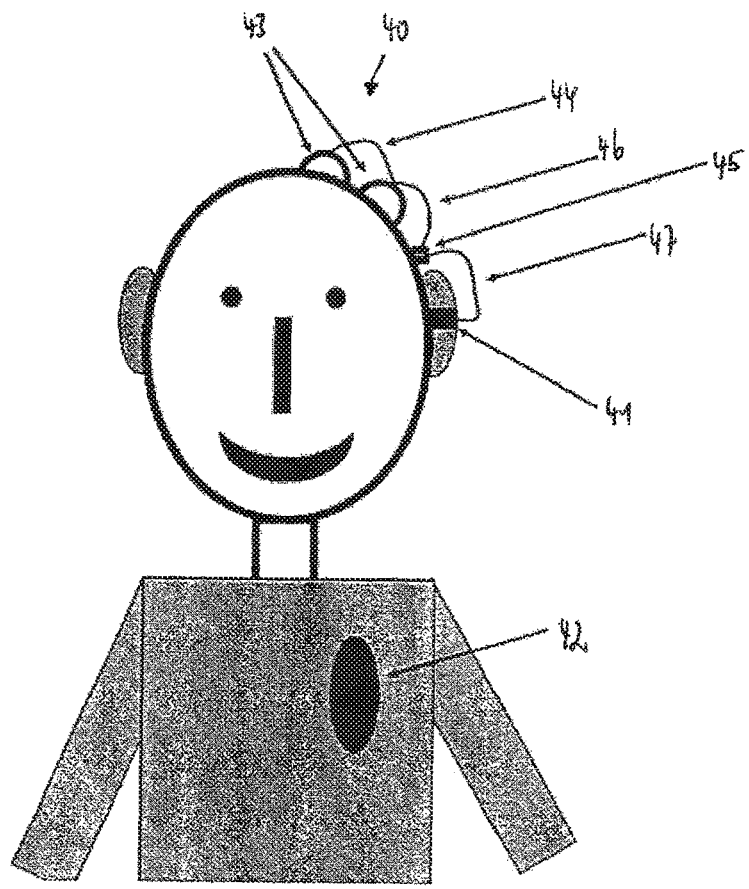
FIG. 4A illustrates a schematic diagram of an apparatus for the acoustic stimulation of neurons with a pathological synchronous and oscillatory neuronal activity.

FIG. 4A schematically shows an apparatus 40 for the non-invasive acoustic stimulation of neurons with a pathological synchronous and oscillatory neuronal activity in accordance with an embodiment of the invention. The acoustic stimuli are administered to the patient via earphones or headphones 41 or by a loudspeaker of different design, wherein an earphone is a loudspeaker placed into the ear canal. The control signals used for this purpose are generated by a control unit 42. Non-invasive fixed EEG electrodes 43 that are connected via a cable 44 serve for the "closed loop" stimulation. The corresponding calculation is carried out in a small component 45 that preferably includes a measurement amplifier and is connected via cables 46, 47 to the EEG electrodes 43 respectively to the earphone or headphone 41 and/or is carried out in the actual control unit 42 housing the battery respectively the rechargeable battery. The control unit 42 and the component 45 are telemetrically connected to one another in the embodiment shown in FIG. 4; in this case the component 45 (or a component connected via a cable) likewise includes a battery respectively a rechargeable battery. Alternatively the control unit 42 and the component 45 could also be connected to one another via a cable in such a way that the component 45 is supplied with energy via the electric power supply of the control unit 42.

Figure 4B:
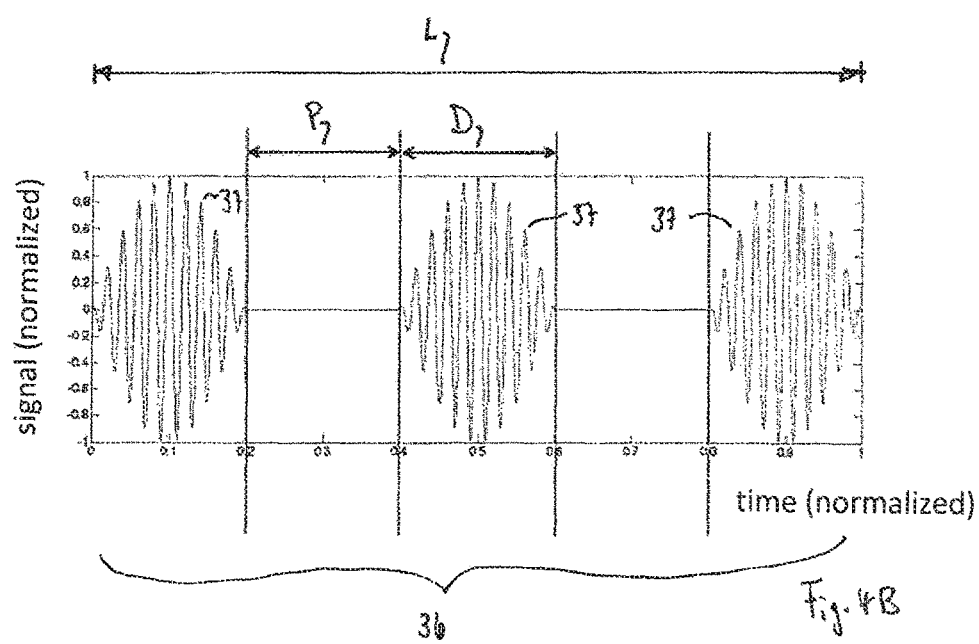
FIG. 4B illustrates a schematic diagram of a burst comprising a plurality of acoustic stimuli.

FIG. 4B as an example shows a burst 36 that can be applied with the apparatus 40. The burst 36 includes three acoustic stimuli following one another configured as individual sounds. In the illustration of FIG. 4B both the stimulation signal as also the time is normalized. For this purpose the maximum of the stimulation signal and the whole duration L of the bursts 36 are respectively set to 1. Each of the stimuli 37 is composed of a high frequency sinusoidal oscillation with a low frequency envelope. The envelope, as shown in FIG. 4B, can be a sinus or a cosine oscillation. However, it can also be a Hanning window, e.g. with cost or a Hamming window or a different window function around which a narrow spectrum is present around the middle frequency, whereas a strong damping effect is achieved outside of the center. By way of the damping at the start and at the end of the respective stimuli 37 noises that appear like a click or a bump to the patient can be avoided.

The frequency of the high frequency sinusoidal oscillation can lie in the range of 200 Hz to 13 kHz. The duration D of a stimuli 37 can for example, lie within a range of 10 ms to 60 ms and the pause P between subsequent stimuli 37 within one burst 36 can lie in the range of 10 ms to 50 ms.

The burst 36 shown in FIG. 4B is configured for the stimulation via a stimulation channel. As described in the following in detail a respective frequency range is associated with the acoustic stimulation of each stimulation channel from which the sounds that are applied as acoustic stimuli in the respective stimulation channels can be selected. Following this the high frequency sinusoidal oscillation of the stimuli 37 shown in FIG. 4A lies in the frequency range of the desired stimulation channel. The stimuli 37 applied in a different stimulation channel have sinusoidal oscillations with other frequencies.

Figure 5:
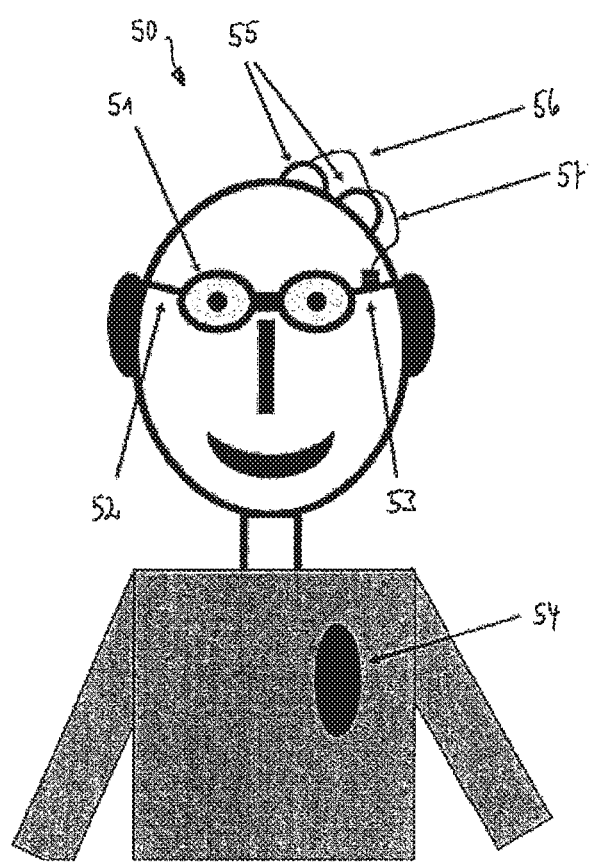
FIG. 5 illustrates a schematic diagram of an apparatus for the visual stimulation of neurons with a pathological synchronous and oscillatory neuronal activity.

FIG. 5 schematically shows an apparatus 50 for the non-invasive visual stimulation of neurons with a pathological synchronous and oscillatory neuronal activity in accordance with an embodiment of the invention. Having regard to this embodiment the patient wears a stimulation pair of glasses 51 that are fastened to the head of the patient e.g. by way of a strap 52. A component 53 comprises a calculation and telemetry unit. The latter serves for the connection to the actual control unit 54 housing the battery respectively the rechargeable battery. The component 53 and the control unit 54 are connected to one another in a telemetric manner; in this case the component 53 (or a component connected thereto via a cable) likewise comprises a battery respectively a rechargeable battery. Alternatively the component 53 and the control unit 54 can also be connected to one another via a cable. Non-invasive fixed EEG electrodes 55 serve for the "closed loop" stimulation. The EEG electrodes 55 are connected via cables 56, 57 to the component 53.

The visual stimuli generated by the stimulation pair of glasses 51 can be based on a brightness variation respectively a luminosity variation (respectively a variation of the light intensity or of the luminous intensity), by way of example, these can be administered as pulses or a sequence of pulses with varying light intensity respectively brightness. The visual stimulation can, depending on the design, be administered as a brightness modulation of natural visual stimuli, e.g. by means of a homogeneous or segmented transmission pair of glasses, with which the transmission can be regulated in a voltage dependent manner as a modulated visual stimuli appearing in addition to a natural visual stimuli, e.g. by means of partially permeable light pair of glasses or as an artificial visual brightness stimuli, e.g. by means of a pair of glasses impermeable to light. The stimulation pair of glasses 51 is preferably divided into different segments whose intensity and/or transmission and/or brightness can be controlled separately of one another in order to stimulate different positions of the retina independent of one another.

Figure 6:
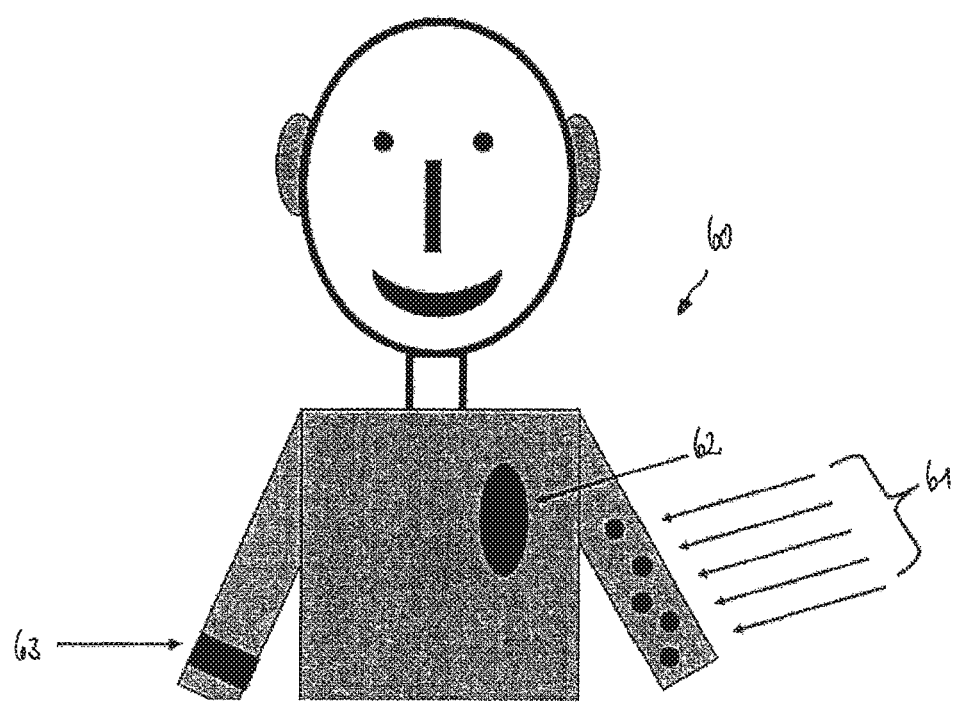
FIG. 6 illustrates a schematic diagram of an apparatus for tactile stimulation, vibratory stimulation, thermal stimulation, transcutaneous electrical stimulation and/or transcutaneous magnetic stimulation and/or ultrasound stimulation of neurons with a pathological synchronous and oscillatory neuronal activity.

FIG. 6 schematically shows an apparatus 60 for non-invasive tactile, vibratory, thermal, transcutaneous electrical and/or transcutaneous magnetic stimulation and/or ultrasound stimulation of neurons with a pathological synchronous and oscillatory neuronal activity in accordance with an embodiment of the invention. The apparatus 60 comprises a stimulation unit 61, a control unit 62 controlling the stimulation unit 61 and an accelerometer (acceleration sensor) 63 for the recording of measurement signals. The stimulation unit 61 and the accelerometer 63 can be connected to the control unit 62 telemetrically or via cable.

The stimulation unit 61 comprises a plurality of stimulation elements for the generation of tactile stimuli, vibratory stimuli, thermal stimuli, transcutaneous electrical stimuli and/or transcutaneous magnetic stimuli and/or ultrasound stimuli. The stimulation elements are configured in such a way that they can be placed on the skin of the patient. Depending on the disease and/or the associated body parts the stimulation elements are fastened in a suitable arrangement at the skin of the patient, for example at the arm, at the leg, at the hand and/or at the foot of the patient. The plurality of stimulation elements enables a stimulation of different receptive regions of the skins via the individual stimulation elements coordinated in time and space.

Stimulation elements for the generation of tactile and/or vibratory stimuli 37 are, for example, vibration actors, that press into the skin of the patient with a frequency in the range of 1 to 300 Hz and in particular of 1 to 60 Hz and preferably of 100 to 300 Hz, i.e. the resonance range of the vibration receptors lying in the skin, and thereby generates the desired stimuli 37. The duration D of each stimulus 37 can, for example, lie in the range of 20 ms to 80 ms and the pause P between successive stimuli 37 within a burst 36 can lie in a range of 15 ms to 40 ms.

Stimulation elements for the generation of thermal stimuli can, for example, be a laser or differently designed elements for the generation of heat, in particular heat radiation. For the generation of transcutaneous electric stimuli typically electrodes are fastened to the skin of the patient. Transcutaneous magnetic stimuli can be generated by corresponding stimulation elements for the generation of magnetic stimuli, in particular current flowing coils. Ultrasound stimuli are generated by stimulation elements for the generation of ultrasound waves.

Having regard to the application of acoustic or visual stimuli these are absorbed by at least one ear respectively at least one eye of the patient. The tactile stimuli, vibratory stimuli, thermal stimuli, transcutaneous electrical stimuli, and/or transcutaneous magnetic stimuli and/or ultrasound stimuli are absorbed by the receptors lying in or beneath the skin and are forwarded to the nervous system. For example, Merkel cells, Ruffini bodies, Meissner bodies and hair follicle receptors count as such receptors that can in particular serve as receptors for the tactile stimuli. The vibratory stimuli predominantly target the depth sensibility. The vibratory stimuli can be absorbed by receptors lying in the skin, the muscles, the sub-cutaneous tissue and/or the tendons of the patient. By way of example the Vater-Pacini bodies shall be mentioned as receptors for the vibratory stimuli, that convey the vibration sense and accelerations. The thermal stimuli can be absorbed by thermal receptors of the skin. These are warm receptors (also referred to as heat receptors, warm sensors or heat sensors) and cold sensors (also referred to as coldness sensors, cold receptors or coldness receptors). In the skin of the human the cold sensors lie more towards the surface, the heat receptors lie a little lower. The transcutaneous electrical and transcutaneous magnetic stimuli, as well as the ultrasound stimuli do not specifically act only on the one group of receptors lying in or under the skin and can moreover also directly stimulate nerve fibers.

The targeted stimulation of certain regions of the brain or of the spinal cord is enabled by way of the tonotopic respectively the somatotopic association of body regions to these regions. For example, acoustic stimuli in the inner ear are transformed into nerve impulses and are forwarded via the hearing nerve to the auditory cortex. By way of the tonotopic arrangement of the auditory cortex a certain part of the auditory cortex is activated by the acoustic stimulation of the inner ear with a certain frequency.

Having regard to the visual stimulation different positions in the viewing field are imaged via the lens of the eye at the different positions of the retina. The different positions of the retina are in turn connected to different neurons in the brain via the optic nerve. Consequently, stimuli applied at the different spatial positions can respectively stimulate different neurons.

Due to somatotopic segmentation of the nerve conductive tracks and associated brain regions, different neurons are furthermore stimulated by way of tactile stimuli, vibratory stimuli, thermal stimuli, transcutaneous electrical stimuli and/or transcutaneous magnetic stimuli and/or ultrasound stimuli that are applied at different positions of the skin. Having regard to these stimulation types the stimulation elements can, for example, be attached at the foot, the lower leg, the upper leg or also at the hand, the lower arm and the upper arm of the patient in order to thereby stimulate certain neurons.

Having regard to the gustatory stimulation different regions of the tongue are stimulated with the corresponding taste qualities—sweet, sour, salty, bitter and umami (Japanese for savoury, spicy, bouillon-like aroma). However, it is also possible to electrically stimulate the tongue. In this case one primarily stimulates the mucous membrane which in the homunculus has a significantly large representation (representation of the surface of the human in the sensomotoric cortex), this means a significantly large associated region is activated. Due to the somatotopic segmentation of the nerve conductive tracks and the associated brain regions different neurons are stimulated by gustatory stimuli that are applied at different positions of the tongue.

In a very general way that is not specifically related to the embodiments described in this context the following is true. Having regard to acoustic stimulation each stimulation channel is associated with a respectively different frequency range from which the sounds, that are applied as acoustic stimuli in the respective stimulation channels, can be selected. Having regard to the visual stimulation, the stimulation passages are determined by different positions or regions in the viewing field of the patient. The visual stimuli generated in the respective stimulation channel are generated in respective positions respectively in a respective region of the viewing field. The stimulation passages of the tactile, vibratory, thermal, transcutaneous electrical and/or transcutaneous magnetic stimuli and/or ultrasound stimuli are stimulated through the positions of the skin which are stimulated with the respective stimulation elements. Consequently, each stimulation channel is associated with the respective position respectively a respective region of the skin.

The stimulation channels of the gustatory stimuli are determined by the positions of the tongue which are stimulated with the corresponding taste qualities or electrical stimuli. Having regard to an olfactory stimulation one uses psychophysically sufficiently disjunct smell stimuli by way of which the stimulation channels can be determined. The psychophysically sufficiently disjunct smell stimuli can e.g. to personalized, this means adapted for the individual patient.

Having regard to transcranial electrical and transcranial magnetic stimuli electrodes respectively magnetic field generators, in particular current conducting coils, are fastened at the body, in particular the head of the patient. By way of electrodes and magnetic field generators currents respectively magnetic fields can be generated in the brain and/or the spinal cord of the patient. Depending on the position of application of the electrodes respectively of the magnetic field generators different target regions in the brain and/or the spinal cord can be stimulated. The stimulation channels are consequently attached at the positions of the body at which the electrodes respectively the magnetic field generators are attached.

The previously described stimulation unit can thus separately stimulate different regions of the brain or of the spinal cord via different stimulation channels, in that the applied stimuli are forwarded via nerve tracks to different target regions that lie in the brain and/or the spinal cord. The target regions can be stimulated during the stimulation with possibly different stimuli and/or stimuli replaced in time.

The invention claimed is:

1. An apparatus for stimulating neurons, the apparatus comprising:
    a non-invasive stimulator configured to generate stimuli in a plurality of stimulation channels that stimulate a neuron population in at least one of a brain and a spinal cord of a patient by the plurality of stimulation channels at respective different points in at least one of the brain and the spinal cord;
    a measurement unit configured to record measurement signals that represent a neuronal activity of the neuron population stimulated with the stimuli; and
    a control unit that controls the stimulator to generate repetitive bursts that each comprise a plurality of stimuli in each of the stimulation channels, wherein the bursts generated in different stimulation channels of the plurality of stimulation channels are delayed in time with respect to one another,
    wherein the stimulator is configured to generate the repetitive bursts such that the repetitive bursts do not reset a phase of the neuronal activity of the respective stimulated neurons,
    wherein the control unit is configured to determine whether the repetitive bursts generated by the stimulator do not reset the phase of the neuronal activity of the respectively stimulated neurons based on the measurement signals,
    wherein, when the control unit determines that the repetitive bursts reset the phase of the neuronal activity of the respectively stimulated neurons, the control unit is further configured to control the stimulator such that subsequently generated bursts have a reduced stimulation strength, and
    wherein the control unit is configured to continue to control the stimulator to subsequently generate bursts having a reduced stimulation strength until the control unit determines that the generated bursts do not reset the phase of the neuronal activity of the respectively stimulated neurons.

2. The apparatus in accordance with claim 1, wherein the stimulator is configured to generate stimuli that are selected from the group of members consisting of acoustic stimuli, visual stimuli, tactile stimuli, vibratory stimuli, olfactory stimuli, gustatory stimuli, transcutaneous electric stimuli, transcutaneous magnetic stimuli, transcranial electrical stimuli, transcranial magnetic stimuli, ultrasound stimuli and combinations thereof.

3. The apparatus in accordance with claim 1, wherein two respective bursts following one another in time and generated in different stimulation channels of the plurality of stimulation channels are delayed in time with respect to one another by $T_{stim}/S$, wherein $T_{stim}=1/f_{stim}$ and $f_{stim}$ is a frequency in the range of 1 to 30 Hz and S being a number of the plurality of stimulation channels.

4. The apparatus in accordance with claim 1, wherein the stimulator is configured to generate the repetitive bursts in a time pattern comprising consecutive cycles that respectively have a duration $T_{stim}$, wherein $T_{stim}=1/f_{stim}$ and $f_{stim}$ is a frequency in the range of 1 to 30 Hz.

5. The apparatus in accordance with claim 4, wherein the stimulator is further configured to generate exactly one burst in one of the cycles in each stimulation channel.

6. The apparatus in accordance with claim 4, wherein each of the consecutive cycles is divided into S sub-cycles and the stimulation unit is further configured to generate no more than one burst in each sub-cycle, with S being a number of the plurality of stimulation channels.

7. The apparatus in accordance with claim 6, wherein each of the consecutive cycles is divided into S sub-cycles of equal length.

8. The apparatus in accordance with claim 4, wherein the stimulator is further configured to periodically generate the repetitive bursts during n successive cycles followed by m cycles in which no stimuli are generated, wherein n and in being non-negative whole numbers.

9. The apparatus in accordance with claim 4, wherein the repetitive bursts are configured to suppress a pathological synchronous and oscillatory activity of the neuron population on an administration to the patient via the plurality of stimulation channels.

10. The apparatus in accordance with claim 9, wherein the duration $T_{stim}$ of a cycle substantially corresponds to the mean period of the pathological oscillation of the neuron population.

11. The apparatus in accordance with claim 1, wherein the control unit is configured to control the stimulator to reduce a stimulation strength of a burst by reducing an amplitude and/or a number of the plurality of the stimuli included in the burst.

12. The apparatus in accordance with claim 1, wherein the control unit is configured to determine whether the repetitive bursts generated by the stimulator do not reset the phase of the neuronal activity of the stimulated neurons by controlling the stimulator to generate a plurality of identical bursts one after the other, and wherein the control unit is further configured to determine the neuronal activity recorded by the measurement unit as a response to each of the plurality of bursts and determines that the bursts do not reset the phase of the neuronal activity of the stimulated neurons when the neuronal activity averaged over all response signals is zero.

13. The apparatus in accordance with claim 1, wherein the control unit is configured to determine whether the repetitive bursts generated by the stimulator do not reset the phase of the neuronal activity of the stimulated neurons by controlling the stimulator to generate a plurality of identical bursts one after the other, and the control unit determines the phase of the neuronal activity recorded by the measurement unit as a response to each of the plurality of bursts and determines that the bursts do not reset the phase of the neuronal activity of the stimulated neurons when the distribution of the phases has no accumulation point.

14. A method for stimulating neurons, the method comprising:
generating, by a non-invasive stimulator, stimuli in a plurality of stimulation channels of the non-invasive stimulator, wherein the stimuli stimulate a neuron population in at least one of a brain and a spinal cord of a patient by the plurality of stimulation channels at respective different points in at least one of the brain and the spinal cord;
recording measurement signals that represent a neuronal activity of the neuron population stimulated with the stimuli;
controlling the non-invasive stimulator by a control unit so as to generate repetitive bursts in each of the stimulation channels with the repetitive bursts each comprising a plurality of stimuli, wherein the bursts generated in different stimulation channels of the plurality of stimulation channels are delayed in time with respect to one another;
determining, based on the measurement signals and by the control unit, whether the repetitive bursts generated by the stimulator do not reset the phase of the neuronal activity of the respectively stimulated neurons;
configuring the control unit the stimulator to generate bursts that have a reduced stimulation strength when the bursts are determined to have reset the phase of the neuronal activity of the respectively stimulated neurons, and continuously reduce the stimulation strength of the bursts until the bursts are determined to not reset the phase of the neuronal activity of the respectively stimulated neurons.

15. The method in accordance with claim 14, further comprising generating the repetitive bursts in a time pattern comprising consecutive cycles that respectively have a duration $T_{stim}$, wherein $T_{stim}=1/f_{stim}$ and $f_{stim}$ is a frequency in the range of 1 to 30 Hz.

16. The method in accordance with claim 14, further comprising:
determining whether the repetitive bursts generated by the stimulator do not reset the phase of the neuronal activity of the stimulated neurons by controlling the stimulator to generate a plurality of identical bursts one after the other;
determining the neuronal activity as a response to each of the plurality of bursts; and
determining that the bursts do not reset the phase of the neuronal activity of the stimulated neurons when the neuronal activity averaged over all response signals is zero.

17. The method in accordance with claim 14, further comprising:
determining whether the repetitive bursts generated by the stimulator do not reset the phase of the neuronal activity of the stimulated neurons by controlling the stimulator to generate a plurality of identical bursts one after the other;
determining the phase of the neuronal activity as a response to each of the plurality of bursts; and
determining that the bursts do not reset the phase of the neuronal activity of the stimulated neurons when the distribution of the phases has no accumulation point.

18. A system for non-invasive neuro-stimulation comprising:
a memory; and
a processor configured to implement instructions stored on the memory for:
generating, by a non-invasive stimulator, stimuli in a plurality of stimulation channels of the non-invasive stimulator, wherein the stimuli stimulate a neuron population in at least one of a brain and a spinal cord of a patient by the plurality of stimulation channels at respective different points in at least one of the brain and the spinal cord;
recording measurement signals that represent a neuronal activity of the neuron population stimulated with the stimuli;
controlling the non-invasive stimulator by a control unit so as to generate repetitive bursts in each of the stimulation channels with the repetitive bursts each comprising a plurality of stimuli, Wherein the bursts generated in different stimulation channels of the plurality of stimulation channels are delayed in time with respect to one another;
determining, based on the measurement signals and by the control unit, whether the repetitive bursts generated by the stimulator do not reset the phase of the neuronal activity of the respectively stimulated neurons;
configuring the control unit the stimulator to generate bursts that have a reduced stimulation strength when the bursts are determined to have reset the phase of the neuronal activity of the respectively stimulated neurons, and continuously reduce the stimulation strength of the bursts until the bursts are determined to not reset the phase of the neuronal activity of the respectively stimulated neurons.

19. The system in accordance with claim 18, wherein the processor is further configured to implement instructions stored on the memory for:
determining whether the repetitive bursts generated by the stimulator do not reset the phase of the neuronal activity of the stimulated neurons by controlling the stimulator to generate a plurality of identical bursts one after the other;
determining the neuronal activity as a response to each of the plurality of bursts; and
determining that the bursts do not reset the phase of the neuronal activity of the stimulated neurons when the neuronal activity averaged over all response signals is zero.

20. The system in accordance with claim 18, wherein the processor is further configured to implement instructions stored on the memory for:
determining whether the repetitive bursts generated by the stimulator do not reset the phase of the neuronal activity of the stimulated neurons by controlling the stimulator to generate a plurality of identical bursts one after the other;

determining the phase of the neuronal activity as a response to each of the plurality of bursts; and determining that the bursts do not reset the phase of the neuronal activity of the stimulated neurons when the distribution of the phases has no accumulation point.

* * * * *